US010709933B2

(12) United States Patent
Tan et al.

(10) Patent No.: US 10,709,933 B2
(45) Date of Patent: Jul. 14, 2020

(54) POSE AND HEART RATE ENERGY EXPENDITURE FOR YOGA

(71) Applicant: Apple Inc., Cupertino, CA (US)

(72) Inventors: Xing Tan, San Jose, CA (US); Karthik Jayaraman Raghuram, Santa Clara, CA (US); Adeeti Ullal, Santa Clara, CA (US); Craig H. Mermel, San Jose, CA (US); Daniel M. Trietsch, Cupertino, CA (US); Alexander Singh Alvarado, Mountain View, CA (US)

(73) Assignee: Apple Inc., Cupertino, CA (US)

( * ) Notice: Subject to any disclaimer, the term of this patent is extended or adjusted under 35 U.S.C. 154(b) by 238 days.

(21) Appl. No.: 15/679,538

(22) Filed: Aug. 17, 2017

(65) Prior Publication Data

US 2018/0050235 A1    Feb. 22, 2018

Related U.S. Application Data

(60) Provisional application No. 62/376,019, filed on Aug. 17, 2016.

(51) Int. Cl.
    *A63B 24/00*   (2006.01)
    *A61B 5/00*    (2006.01)
    (Continued)

(52) U.S. Cl.
    CPC ...... *A63B 24/0062* (2013.01); *A61B 5/02416* (2013.01); *A61B 5/1116* (2013.01);
    (Continued)

(58) Field of Classification Search
    CPC .......... A63B 24/0062; A63B 2220/836; A63B 2225/50; A61B 5/02416; A61B 5/1116;
    (Continued)

(56) References Cited

U.S. PATENT DOCUMENTS

| 4,566,461 A | 1/1986 | Lubell et al. |
| 5,158,093 A | 10/1992 | Shvartz et al. |

(Continued)

FOREIGN PATENT DOCUMENTS

| GB | 2465824 | 6/2010 |
| JP | 2015-051333 A | 3/2010 |

(Continued)

OTHER PUBLICATIONS

Your Fitness FAQ, Why is it important to warm up and cool down in a workout?, 2012, Web, Retrieved from: http://www.yourfitnessfaq.com/whyisitimportanttowarmupandcooldowninaworkout.html.

(Continued)

*Primary Examiner* — Regis J Betsch
(74) *Attorney, Agent, or Firm* — DLA Piper LLP (57) ABSTRACT

A method and a system for determining an energy expenditure of a user while practicing yoga are described. A heart rate sensing module can measure the user's heart rate. A temperature sensing module can measure ambient temperature. A motion sensing module can collect user's motion data. In some embodiments, a hot yoga session can be detected based on measured ambient temperature. In some embodiments, a yoga type can be detected based on the motion data. In some embodiments, an energy expenditure model can be applied based on the determined yoga type.

20 Claims, 7 Drawing Sheets

(51) Int. Cl.
*A61B 5/11* (2006.01)
*A61B 5/024* (2006.01)

(52) U.S. Cl.
CPC ............ *A61B 5/1118* (2013.01); *A61B 5/681* (2013.01); *A61B 5/6898* (2013.01); *A61B 2503/10* (2013.01); *A61B 2560/0252* (2013.01); *A61B 2562/0219* (2013.01); *A63B 2220/836* (2013.01); *A63B 2225/50* (2013.01)

(58) Field of Classification Search
CPC ..... A61B 5/1118; A61B 5/681; A61B 5/6898; A61B 2503/10; A61B 2560/0252; A61B 2562/0219
See application file for complete search history.

(56) References Cited

U.S. PATENT DOCUMENTS

| | | | |
|---|---|---|---|
| 6,013,008 | A | 1/2000 | Fukushima |
| 6,059,724 | A | 5/2000 | Campell et al. |
| 6,582,380 | B2 | 6/2003 | Kazlausky et al. |
| 6,687,535 | B2 | 2/2004 | Hautala et al. |
| 6,837,827 | B1 | 1/2005 | Lee et al. |
| 6,868,338 | B1 | 3/2005 | Elliott |
| 7,254,516 | B2 | 8/2007 | Case, Jr. et al. |
| 7,467,060 | B2 | 12/2008 | Kulach et al. |
| 7,534,206 | B1 | 5/2009 | Lovitt et al. |
| 7,690,556 | B1 | 4/2010 | Kahn et al. |
| 7,771,320 | B2 | 8/2010 | Riley et al. |
| 7,805,149 | B2 | 9/2010 | Werner et al. |
| 7,841,967 | B1 | 11/2010 | Kahn et al. |
| 8,290,480 | B2 | 10/2012 | Abramson et al. |
| 8,483,775 | B2 | 7/2013 | Buck et al. |
| 8,589,174 | B2 | 11/2013 | Nelson et al. |
| 8,892,391 | B2 | 11/2014 | Tu et al. |
| 8,894,576 | B2 | 11/2014 | Alwan et al. |
| 8,911,329 | B2 | 12/2014 | Lin et al. |
| 9,413,871 | B2 | 8/2016 | Nixon et al. |
| 9,526,430 | B2 | 12/2016 | Srinivas et al. |
| 9,788,794 | B2 | 10/2017 | Le Boeuf et al. |
| 10,188,347 | B2 | 1/2019 | Self et al. |
| 10,206,627 | B2 | 2/2019 | Le Boeuf et al. |
| 10,219,708 | B2 | 3/2019 | Altini |
| 10,292,606 | B2 | 5/2019 | Wisbey et al. |
| 2002/0019585 | A1 | 2/2002 | Dickinson |
| 2003/0032460 | A1 | 2/2003 | Cannon et al. |
| 2003/0138763 | A1 | 7/2003 | Roncalez et al. |
| 2004/0064061 | A1 | 4/2004 | Nissila |
| 2005/0107723 | A1 | 5/2005 | Wehman et al. |
| 2006/0136173 | A1 | 6/2006 | Case et al. |
| 2006/0217231 | A1 | 9/2006 | Parks et al. |
| 2007/0100666 | A1* | 5/2007 | Stivoric ................... G05B 1/01 705/3 |
| 2007/0219059 | A1 | 9/2007 | Schwartz et al. |
| 2007/0275825 | A1 | 11/2007 | O'Brien |
| 2008/0096726 | A1* | 4/2008 | Riley ................ A63B 24/0006 482/8 |
| 2008/0214360 | A1 | 9/2008 | Stirling et al. |
| 2009/0009320 | A1 | 1/2009 | O'Connor et al. |
| 2009/0043531 | A1 | 2/2009 | Kahn et al. |
| 2010/0130890 | A1 | 5/2010 | Matsumura et al. |
| 2010/0204952 | A1 | 8/2010 | Irlam et al. |
| 2010/0210953 | A1 | 8/2010 | Sholder et al. |
| 2010/0210975 | A1 | 8/2010 | Anthony, III et al. |
| 2010/0217099 | A1 | 8/2010 | LeBoeuf et al. |
| 2010/0298656 | A1 | 11/2010 | McCombie et al. |
| 2011/0040193 | A1 | 2/2011 | Seppanen et al. |
| 2011/0054359 | A1 | 3/2011 | Sazonov et al. |
| 2011/0131012 | A1 | 6/2011 | Czaja et al. |
| 2011/0152695 | A1 | 6/2011 | Granqvist et al. |
| 2011/0195707 | A1 | 8/2011 | Faerber et al. |
| 2011/0238485 | A1 | 9/2011 | Haumont et al. |
| 2012/0083715 | A1 | 4/2012 | Yuen et al. |
| 2012/0172677 | A1 | 7/2012 | Logan et al. |
| 2012/0238832 | A1 | 9/2012 | Jang et al. |
| 2012/0296455 | A1 | 11/2012 | Ohnemus et al. |
| 2013/0023739 | A1 | 1/2013 | Russel |
| 2013/0096943 | A1 | 4/2013 | Carey et al. |
| 2013/0158686 | A1 | 6/2013 | Zhang et al. |
| 2013/0178335 | A1 | 7/2013 | Lin et al. |
| 2013/0197377 | A1 | 8/2013 | Takahiko et al. |
| 2013/0267794 | A1 | 10/2013 | Fernstrom et al. |
| 2014/0073486 | A1 | 3/2014 | Ahmed et al. |
| 2014/0087708 | A1 | 3/2014 | Kalita et al. |
| 2014/0088444 | A1 | 3/2014 | Saalasti et al. |
| 2014/0107932 | A1 | 4/2014 | Luna |
| 2014/0109390 | A1 | 4/2014 | Manning |
| 2014/0121471 | A1* | 5/2014 | Walker ................ A61B 5/1128 600/301 |
| 2014/0167973 | A1 | 6/2014 | Letchner et al. |
| 2014/0172238 | A1 | 6/2014 | Craine |
| 2014/0197946 | A1 | 7/2014 | Park et al. |
| 2014/0200906 | A1 | 7/2014 | Bentley et al. |
| 2014/0207264 | A1 | 7/2014 | Quy |
| 2014/0213920 | A1 | 7/2014 | Lee et al. |
| 2014/0221854 | A1 | 8/2014 | Wai |
| 2014/0228649 | A1 | 8/2014 | Rayner et al. |
| 2014/0244071 | A1 | 8/2014 | Czaja et al. |
| 2014/0266789 | A1 | 9/2014 | Matus |
| 2014/0276127 | A1 | 9/2014 | Ferdosi et al. |
| 2014/0278139 | A1 | 9/2014 | Hong et al. |
| 2014/0278229 | A1* | 9/2014 | Hong .................... A63B 71/06 702/160 |
| 2014/0316305 | A1* | 10/2014 | Venkatraman ........ A61B 5/1112 600/595 |
| 2015/0087929 | A1 | 3/2015 | Rapoport et al. |
| 2015/0088006 | A1 | 3/2015 | Rapoport et al. |
| 2015/0100141 | A1 | 4/2015 | Hughes |
| 2015/0119728 | A1 | 4/2015 | Blackadar et al. |
| 2015/0250417 | A1 | 9/2015 | Cheng et al. |
| 2015/0256689 | A1 | 9/2015 | Erkkila et al. |
| 2015/0260514 | A1 | 9/2015 | Menelas et al. |
| 2015/0327804 | A1 | 11/2015 | Lefever et al. |
| 2015/0328523 | A1 | 11/2015 | Heling et al. |
| 2015/0338926 | A1 | 11/2015 | Park et al. |
| 2015/0345985 | A1 | 12/2015 | Fung et al. |
| 2015/0357948 | A1 | 12/2015 | Goldstein |
| 2015/0374240 | A1 | 12/2015 | Lee |
| 2016/0021238 | A1 | 1/2016 | Abramson et al. |
| 2016/0057372 | A1 | 3/2016 | Raghuram et al. |
| 2016/0058302 | A1 | 3/2016 | Raghuram et al. |
| 2016/0058329 | A1 | 3/2016 | Srinivas et al. |
| 2016/0058332 | A1 | 3/2016 | Tan et al. |
| 2016/0058333 | A1 | 3/2016 | Arnold et al. |
| 2016/0058356 | A1 | 3/2016 | Raghuram et al. |
| 2016/0058370 | A1 | 3/2016 | Raghuram et al. |
| 2016/0058371 | A1* | 3/2016 | Singh Alvarado ... A61B 5/0205 600/483 |
| 2016/0058372 | A1* | 3/2016 | Raghuram ............ A61B 5/0205 600/595 |
| 2016/0084869 | A1 | 3/2016 | Yuen et al. |
| 2016/0170998 | A1 | 6/2016 | Frank et al. |
| 2016/0206249 | A1 | 7/2016 | Sartor et al. |
| 2016/0256058 | A1 | 9/2016 | Pham et al. |
| 2016/0269572 | A1 | 9/2016 | Erkkila et al. |
| 2016/0287177 | A1 | 10/2016 | Huppert et al. |
| 2016/0361020 | A1 | 12/2016 | LeBoeuf et al. |
| 2016/0374614 | A1 | 12/2016 | Cavallaro et al. |
| 2017/0007166 | A1 | 1/2017 | Roover et al. |
| 2017/0061817 | A1 | 3/2017 | Mettler May |
| 2017/0074897 | A1 | 3/2017 | Mermel et al. |
| 2017/0082649 | A1 | 3/2017 | Tu et al. |
| 2017/0094450 | A1 | 3/2017 | Tu et al. |
| 2017/0111768 | A1 | 4/2017 | Smith et al. |
| 2017/0188893 | A1 | 7/2017 | Venkatraman et al. |
| 2017/0202486 | A1 | 7/2017 | Martikka et al. |
| 2017/0259116 | A1* | 9/2017 | Mestas ............... A63B 24/0062 |
| 2017/0273619 | A1 | 9/2017 | Alvarado et al. |
| 2017/0347885 | A1 | 12/2017 | Tan et al. |
| 2017/0367658 | A1 | 12/2017 | LeBoeuf et al. |
| 2018/0028863 | A1 | 2/2018 | Matsuda |
| 2018/0049694 | A1 | 2/2018 | Singh Alvarado et al. |

(56) References Cited

U.S. PATENT DOCUMENTS

FOREIGN PATENT DOCUMENTS

| JP | 2013-39316 A | 2/2013 |
| JP | 2014-42757 A | 3/2014 |
| JP | 2016-150018 A | 8/2016 |
| JP | 2018-000543 A | 1/2018 |
| JP | 2018-015187 A | 2/2018 |
| WO | 2010090867 | 8/2010 |
| WO | 2011/105914 A1 | 9/2011 |
| WO | 2015/126182 A | 8/2015 |

OTHER PUBLICATIONS

Vella et al, Exercise After-Burn: Research Update, 2005, Web, Retrieved from: http://www.unm.edu/~lkravitz/Article%20folder/epocarticle.html.

Song et al., "Training Activity Recognition Systems Online Using Real-Time Crowdsourcing", University of Rochester Computer Science, UbiCom' 12, Sep. 5-8, 2012 (2 pages).

Rowlands et al., "Assessing Sedentary Behavior with the GENEActiv: Introducing the Sedentary Sphere". Medicine and science in sports and exercise 46.6 (2014): 1235-1247.

Hasson et al., "Accuracy of four resting metabolic rate production equations: Effects of sex, body mass index, age, and race/ethnicity", Journal of Science and Medicine in Sport, 2011, vol. 14, p. 344-351.

Lucas et al., "Mechanisms of orthostatic intolerance following very prolonged exercise", 2008, J Appl Physiol, 105: 213-225.

Kunze et al., "Where am i: Recognizing on-body positions of wearable sensors." Location-and context-awareness. Springer Berlin Heidelberg, 2005. 264-275.

Keytel et al., "Prediction of energy expenditure from heart rate monitoring during submaximal exercise", 2005, Journal of Sports Sciences, 23(3):289-97.

Sabatini, Kalman-filter orientation determination using inertial/magnetic sensors: observability analysis and performance evaluation, Sep. 27, 2011, Sensors 2011, 11, 9182-9206.

Jackson et al., "Prediction of functional aerobic capacity without exercise testing", Medicine and Science in Sports and Exercise, 22(6), 863-870, 1990.

Isaacs et al., "Modeling energy expenditure and oxygen consumption in human exposure models: accounting for fatigue and EPOC", 2008, Journal of Exposure Science and Environmental Epidemiology, 18: 289-298.

Human Kinetics, Aerobic Workout Components, 2011, Web, Retrieved from: http://www.humankinetics.com/excerpts/excerpts/aerobicworkoutcomponentsexcerpt.

Gao et al., "Evaluation of accelerometer based multi-sensor versus single-sensor activity recognition systems." Medical engineering & physics 36.6 (2014): 779-785.

Frankenfield et al., "Comparison of Predictive Equations for Resting Metabolic Rate in Healthy Nonobese and Obese adults: A systematic review". Journal of the American Dietetic Association. May 2005, vol. 105, No. 5, p. 775-789.

Chu, "In-Vehicle Driver Detection Using Mobile Phone Sensors", Submitted for Graduation with departmental Distinction in Electrical and Computer Engineering, Apr. 20, 2011, pp. 1-21.

Bo et al., "TEXIVE: Detecting Drivers Using Personal Smart Phones by Leveraging Inertial Sensors", Department of Computer Science, Illinois Institute of Technology, Chicago IL, Dec. 7, 2014, pp. 1-12.

Brooks, G.A. et al., "Exercise Physiology: Human Bioenergetics and Its Applications," Fourth Edition, McGraw Hill, ISBN 0-07-255642-0, Chapter 2: Bioenergetics, Chapter 10: Metabolic Response to Exercise: Lactate Metabolism During Exercise and Recovery, Excess Postexercise O2 Consumption (EPOC), O2 Deficit, O2 Debt, and the Anaerobic Threshold, Chapter 16: Cardiovascular Dynamics During Exercise, Chapter 21: Principles of Endurance Conditioning, Chapter 27: Exercise Testing and Prescription, 141 pages (2004).

Noakes, Timothy D., "Lore of Running," Fourth Edition, Human Kinetics, Chapter 2: Oxygen Transport and Running Economy, Chapter 3: Energy Systems and Running Performance, 157 pages (2002).

Rapoport, Benjamin I., "Metabolic Factors Limiting Performance in Marathon Runners," PLoS Computational Biology, vol. 6, Issue 10, 13 pages (Oct. 2010).

Tanaka, H. et al., "Age-predicted maximal heart rate revisited," Journal of the American College of Cardiology, vol. 37, Issue 1, pp. 153-156 (Jan. 2001).

Wang, L. et al., "Time constant of heart rate recovery after low level exercise as a useful measure of cardiovascular fitness," Conf. Proc. IEEE Eng. Med. Biol. Soc., vol. 1, pp. 1799-1802 (2006).

Le, et al., "Sensor-based Training Optimization of a Cyclist Group", Seventh International Conference on Hybrid Intelligent Systems, IEEE 2007, pp. 265-270.

Yamaji, et al., "Relationship Between Heart Rate and Relative Oxygen Intake in Male Subjects Aged 10 to 27 Years", J. Human Ergol., 7:29-39, Jan. 27, 1978.

Novatel, "IMU Error and Their Effects", Novatel Application Notes APN-064 Rev A p. 1-6, Feb. 21, 2014.

KINprof, May 31, 2011, Predictive VO2max tests, Web Video, Retrieved from: https://www.youtube.com/watch?v=_9e3HcY1sm8.

PCT International Application No. PCT/US2017/049693, International Search Report dated Aug. 12, 2017, 3 pages.

International Search Report and Written Opinion received for PCT Patent Application No. PCT/US2018/047290, dated Nov. 8, 2018, 14 pages.

Bruce, R.A. et al., "Exercising testing in adult normal subjects and cardiac patients," Pediatrics, vol. 32, No. Suppl., pp. 742-756 (Oct. 1963).

Bruce, R.A. et al., "Maximal oxygen intake and nomographic assessment of functional aerobic impairment in cardiovascular disease," American Heart Journal, vol. 85, Issue 4, pp. 546-562 (Apr. 1973).

Burke, Edmund R., "High-Tech Cycling," Second Edition, Human Kinetics, Chapter 4: Optimizing the Crank Cycle and Pedaling Cadence, Chapter 5: Cycling Biomechanics, Chapter 6: Cycling Power, Chapter 10: Physiology of Professional Road Cycling, Chapter 11: Physiology of Mountain Biking, 131 pages (2003).

Cavanagh, P.R. et al., "The effect of stride length variation on oxygen uptake during distance running," Medicine and Science in Sports and Exercise, vol. 14, No. 1, pp. 30-35 (1982).

Earnest, C.P. et al., "Cross-sectional association between maximal estimated cardiorespiratory fitness, cardiometabolic risk factors and metabolic syndrome for men and women in the Aerobics Center Longitudinal Study," Mayo Clin Proceedings, vol. 88, No. 3, pp. 259-270, 20 pages (Mar. 2013).

Fox, S.M. et al., "Physical Activity and the Prevention of Coronary Heart Disease," Bull. N.Y. Acad. Med., vol. 44, No. 8, pp. 950-967 (Aug. 1968).

Glass, S., et al., "ACSM's Metabolic Calculations Handbook," Lippincott Williams & Wilkins, 124 pages (2007).

Lavie, C.J. et al., "Impact of cardiorespiratory fitness on the obesity paradox in patients with heart failure," Mayo Clinic Proceedings, vol. 88, No. 3, pp. 251-258 (Mar. 2013).

Margaria, R. et al., "Energy cost of running," Journal of Applied Physiology, vol. 18, No. 2, pp. 367-370 (Mar. 1, 1963).

Myers, J. et at., "Exercise Capacity and Mortality Among Men Referred for Exercise Testing," The New England Journal of Medicine, vol. 346, No. 11, pp. 793-801 (Mar. 14, 2002).

McArdle, W.D. et al., "Exercise Physiology: Nutrition, Energy and Human Performance", Seventh Edition, Lippincott Williams & Wilkins, 2010, Chapters 5-11 and 21, pp. 118-251 and 451-489.

\* cited by examiner

POSE AND HEART RATE ENERGY EXPENDITURE FOR YOGA

CROSS-REFERENCE TO RELATED APPLICATION

This application claims priority to and the benefit of U.S. Provisional Application No. 62/376,019 filed on Aug. 17, 2016, the disclosure of which is incorporated by reference herein by its entirety.

FIELD

The present disclosure relates generally to improving calorie expenditure prediction and tracking and, more particularly, to techniques for determining energy expenditure based on a user's poses and heart rate in yoga.

BACKGROUND

Heart rate and energy expenditure are usually linearly correlated during high intensity workouts in traditional aerobic activities. Traditional aerobic activities, such as running, swimming, or cycling, are usually performed with a relatively constant body pose. That is, a user's torso and limbs are in a relatively constant position throughout the activity. The relationship between heart rate and energy expenditure can be more complicated when a user's poses during exercise are more variable.

SUMMARY

The present disclosure relates to a method for improving the accuracy of a wearable device while calculating an energy expenditure of a user practicing yoga. In some embodiments, the method can include: detecting, by a processor circuit of a wearable device, a start of a yoga session; measuring, by a heart rate sensing module of the wearable device, a heart rates of the user, wherein the heart rate sensing module comprises a photoplethysmogram (PPG) sensor and the PPG sensor is configured to be worn adjacent to the user's skin; measuring, by a temperature sensing module of the wearable device, ambient temperature; collecting, by a motion sensing module of the wearable device, motion data of the user; determining by the processor circuit, a type of yoga practiced by the user based on the measured ambient temperature and the collected motion data; selecting an energy expenditure model associated with the determined type of yoga; detecting an end of the yoga session; calculating an energy expenditure of the user based on at least the measured heart rate and the selected energy expenditure model; and outputting the calculated energy expenditure of the user during the yoga session.

In some embodiments, the wearable device can detect a start of a yoga session after receiving an instruction from the user. In some embodiments, the wearable device can detect a start of a yoga session by receiving location data of the wearable device and comparing the received location data with a pre-determined location. If the received location data matches a pre-determined location, the wearable device can determine a start of a yoga session.

In some embodiments, the wearable device can measure a first ambient temperature prior to the start of the yoga session, and measure a second ambient temperature within a pre-defined time period proximate to the start of the yoga session. The wearable device can determine a change of ambient temperature between the first ambient temperature and the second ambient temperature, and can compare the change of ambient temperature with a pre-defined temperature change threshold. In some embodiments, the pre-defined temperature change threshold is substantially 20 degrees Fahrenheit. In some embodiments, if the change of ambient temperature is greater than the pre-defined temperature change threshold, the wearable device can determine the user is practicing hot yoga.

In some embodiments, the wearable device can compare the measured ambient temperature with a pre-defined temperature threshold. In some embodiments, the pre-defined temperature threshold is substantially 100 degrees Fahrenheit. In some embodiments, if the measured ambient temperature is greater than the pre-defined temperature threshold, the wearable device can determine the user is practicing hot yoga. In some embodiments, the method can include measuring humidity by a humidity sensing module of the wearable device. The wearable device can compare the measured humidity with a pre-determined humidity threshold. If the measured humidity is greater than the pre-determined humidity threshold, the wearable device can determine the user is practicing hot yoga.

In some embodiments, the type of yoga can include power yoga, wellness yoga, hot yoga, or meditative yoga. In some embodiments, the motion sensing module can include at least one of an accelerometer, a gyroscope, and a magnetometer.

The present disclosure also relates to a system for improving the accuracy of a wearable device while calculating an energy expenditure of a user practicing yoga. In some embodiments, the system can include: a heart rate sensing module configured to measure a heart rate of the user, wherein the heart rate sensing module comprises a photoplethysmogram (PPG) sensor and the PPG sensor is configured to be worn adjacent to the user's skin; a temperature sensing module configured to measure ambient temperature; a motion sensing module configured to collect motion data of the user; a processor circuit in communication with the heart rate sensing module, the temperature sensing module, and the motion sensing module, the processor circuit configured to execute instructions causing the processor circuit to: detect a start of a yoga session; determine a type of yoga practiced by the user based on the measured ambient temperature and the collected motion data; select an energy expenditure model associated with the determined type of yoga; detect an end of the yoga session; calculate an energy expenditure of the user based on at least the measured heart rate and the selected energy expenditure model; and output the calculated energy expenditure of the user.

BRIEF DESCRIPTION OF THE DRAWINGS

Various objectives, features, and advantages of the disclosed subject matter can be more fully appreciated with reference to the following detailed description of the disclosed subject matter when considered in connection with the following drawings, in which like reference numerals identify like elements.

DETAILED DESCRIPTION

Systems and methods are disclosed herein to calibrate heart rate measurements during a user's exercise session based on a type of user's motion data and ambient temperature data in order to better estimate energy expenditure during the exercise session. In some embodiments of the present disclosure, the systems and methods disclosed herein are used to detect a type of yoga session being practiced by a user and to calibrate heart rate measurements detected during the yoga session.

Figure 1:
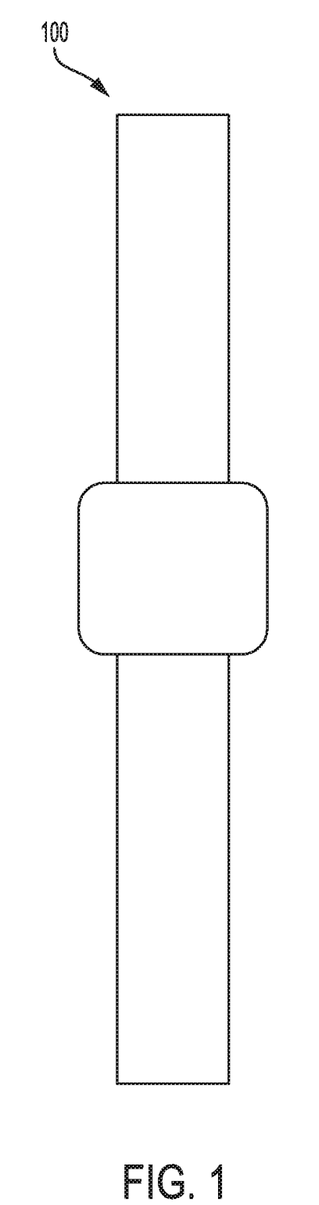
FIG. 1 shows an example of a fitness tracking device (or a "wearable device") 100, according to some embodiments of the present disclosure.

FIG. 1 shows an example of a fitness tracking device (or a "wearable device") 100, according to some embodiments of the present disclosure. In some embodiments, the fitness tracking device 100 may be a wearable device, such as a watch configured to be worn around an individual's wrist. As described in more detail below, the fitness tracking device 100 may be calibrated according to physical attributes of the individual and physical activity by the individual user who is wearing the fitness tracking device 100, including, for example, heart rate statistics.

Figure 2:
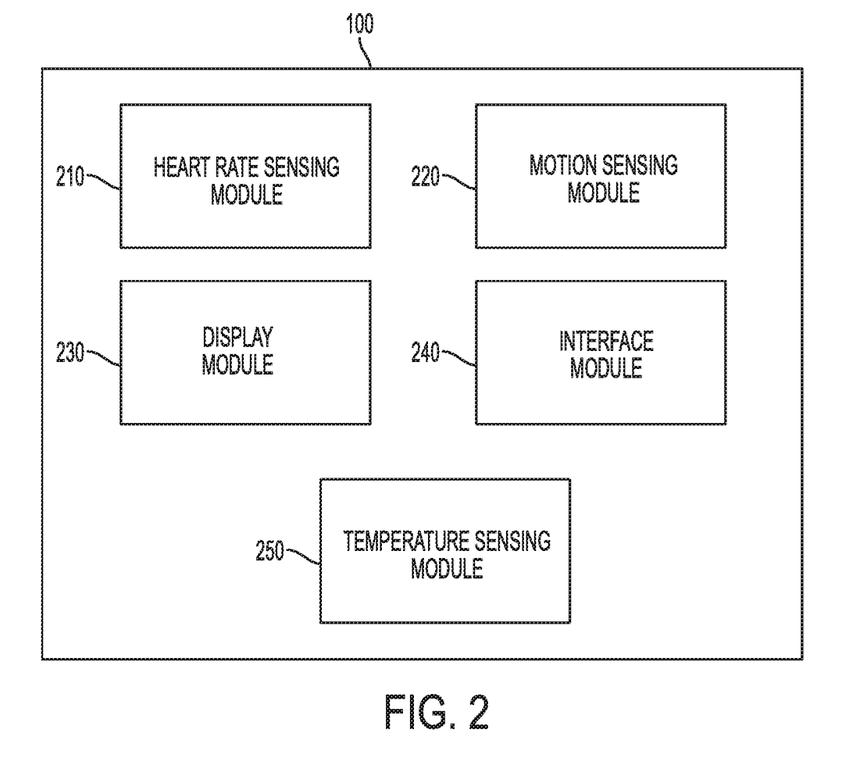
FIG. 2 depicts a block diagram of example components that may be found within the fitness tracking device 100, according to some embodiments of the present disclosure.

FIG. 2 depicts a block diagram of example components that may be found within the fitness tracking device 100, according to some embodiments of the present disclosure. These components may include a heart rate sensing module 210, a motion sensing module 220, a display module 230, an interface module 240, and a temperature sensing module 250.

The heart rate sensing module 210 may include or may be in communication with a photoplethysmogram "PPG" sensor as previously described. The fitness tracking device 100 can measure an individual's current heart rate from the PPG. The heart rate sensor may also be configured to determine a confidence level indicating a relative likelihood of an accuracy of a given heart rate measurement. In other embodiments, a traditional heart rate monitor may be used and may communicate with the fitness tracking device 100 through a near field communication method (e.g., Bluetooth).

The fitness tracking device 100 may include an LED and a photodiode or the equivalent to obtain PPG data. The fitness tracking device 100 may subsequently determine the user's current heart rate based on the PPG data.

To conserve battery power on the fitness tracking device 100, the LED may be a relatively low-power LED, such as a green LED. In some embodiments, to further conserve power on the fitness tracking device 100, the fitness tracking device 100 may be configured to check heart rate at periodic intervals (e.g., once per minute, or once per three minutes). The period for checking heart rate may change dynamically. For example, if the fitness tracking device 100 automatically detects or receives input from the user that the user is engaged in a certain level, intensity, or type of physical activity (e.g., "in session"), the fitness tracking device may check heart rate more frequently (e.g., once per thirty seconds, once per minute, etc.). The fitness tracking device 100 may use, for example, machine learning techniques, battery power monitoring, or physical activity monitoring to balance the frequency of heart rate samples for accurate calorimetry with power optimization.

In addition to the heart rate sensing module 210, the fitness tracking device 100 may also include the motion sensing module 220. The motion sensing module 220 may include one or more motion sensors, such as an accelerometer or a gyroscope. In some embodiments, the accelerometer may be a three-axis, microelectromechanical system (MEMS) accelerometer, and the gyroscope may be a three-axis MEMS gyroscope. A microprocessor (not shown) or motion coprocessor (not shown) of the fitness tracking device 100 may receive motion information from the motion sensors of the motion sensing module 220 to track acceleration, rotation, position, or orientation information of the fitness tracking device 100 in six degrees of freedom through three-dimensional space.

In some embodiments, the motion sensing module 220 may include other types of sensors in addition to accelerometers and gyroscopes. For example, the motion sensing module 220 may include an altimeter or barometer, or other types of location sensors, such as a GPS sensor.

In some embodiments, the fitness tracking device 100 may include a temperature sensing module 250. The temperature sensing module 250 can measure both the ambient temperature proximate to fitness tracking device 100 as well a temperature of a user wearing the fitness tracking device 100. In some embodiments, the temperature sensing module 250 includes a humidity level sensor. As described in more detail below, a microprocessor (not shown) or motion coprocessor (not shown) of the fitness tracking device 100 may receive temperature information from the temperature sensing module 250 to determine a user's location and activity (e.g., practicing yoga in a high temperature room) by calculating a temperature differential of a user's environment at different times. In some embodiments, the microprocessor (not shown) or motion coprocessor (not shown) of the fitness tracking device 100 may receive temperature information from a temperature sensor in a companion device, such as the companion device 300 shown in FIG. 3.

In some embodiments, the fitness tracking device 100 may take advantage of the knowledge that the heart rate sensing module 210 and the motion sensing module 220 are approximately co-located in space and time to combine data from each module 210 and 220 to improve the accuracy of its calorimetry functionality. Depending on the current activity and a determination of a confidence of current heart rate and motion data, the fitness tracking device 100 may also rely on one of either the heart rate or a motion-derived work rate to estimate energy expenditure more accurately.

The fitness tracking device 100 may also include a display module 230. Display module 230 may be a screen, such as a crystalline (e.g., sapphire) or glass touchscreen, configured to provide output to the user as well as receive input form the user via touch. For example, display 230 may be configured to display a current heart rate or a daily average energy expenditure. Display module 230 may receive input from the user to select, for example, which information should be displayed, or whether the user is beginning a physical activity (e.g., starting a session) or ending a physical activity (e.g., ending a session), such as a running session or a cycling session. In some embodiments, the fitness tracking device 100 may present output to the user in other ways, such as by producing sound with a speaker (not shown), and the fitness tracking device 100 may receive input from the user in other ways, such as by receiving voice commands via a microphone (not shown).

In some embodiments, the fitness tracking device 100 may communicate with external devices via interface module 240, including a configuration to present output to a user or receive input from a user. Interface module 240 may be a wireless interface. The wireless interface may be a standard Bluetooth (IEEE 802.15) interface, such as Bluetooth v4.0, also known as "Bluetooth low energy." In other embodiments, the interface may operate according to a cellphone network protocol such as LTE or a Wi-Fi (IEEE 802.11) protocol. In other embodiments, interface module 240 may include wired interfaces, such as a headphone jack or bus connector (e.g., Lightning, Thunderbolt, USB, etc.).

The fitness tracking device 100 may be configured to communicate with a companion device 300 (FIG. 3), such as a smartphone, as described in more detail herein. In some embodiments, the fitness tracking device 100 may be configured to communicate with other external devices, such as a notebook or desktop computer, tablet, headphones, Bluetooth headset, etc.

The modules described above are examples, and embodiments of the fitness tracking device 100 may include other modules not shown. For example, the fitness tracking device 100 may include one or more microprocessors (not shown) for processing heart rate data, motion data, other information in the fitness tracking device 100, or executing instructions for firmware or apps stored in a non-transitory processor-readable medium such as a memory module (not shown). Additionally, some embodiments of the fitness tracking device 100 may include a rechargeable battery (e.g., a lithium-ion battery), a microphone or a microphone array, one or more cameras, one or more speakers, a watchband, a crystalline (e.g., sapphire) or glass-covered scratch-resistant display, water-resistant casing or coating, etc.

Figure 3:
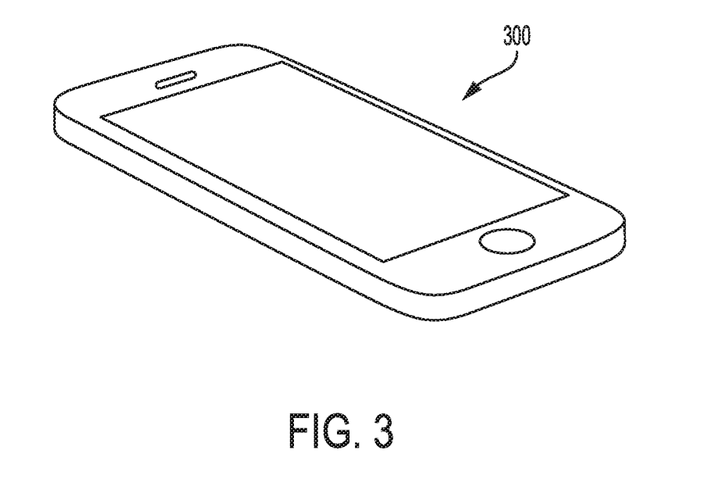
FIG. 3 shows an example of a companion device 300, according to some embodiments of the present disclosure.

FIG. 3 shows an example of a companion device 300, according to some embodiments of the present disclosure. The fitness tracking device 100 may be configured to communicate with the companion device 300 via a wired or wireless communication channel (e.g., Bluetooth, Wi-Fi, etc.). In some embodiments, the companion device 300 may be a smartphone, tablet, or similar portable computing device. The companion device 300 may be carried by the user, stored in the user's pocket, strapped to the user's arm with an armband or similar device, placed on a table, or otherwise positioned within communicable range of the fitness tracking device 100.

The companion device 300 may include a variety of sensors, such as location and motion sensors (not shown). When the companion device 300 may be optionally available for communication with the fitness tracking device 100, the fitness tracking device 100 may receive additional data from the companion device 300 to improve or supplement its calibration or calorimetry processes. For example, in some embodiments, the fitness tracking device 100 may not include a GPS sensor as opposed to an alternative embodiment in which the fitness tracking device 100 may include a GPS sensor. In the case where the fitness tracking device 100 may not include a GPS sensor, a GPS sensor of the companion device 300 may collect GPS location information, and the fitness tracking device 100 may receive the GPS location information via interface module 240 (FIG. 2) from the companion device 300.

In another example, the fitness tracking device 100 may not include an altimeter, as opposed to an alternative embodiment in which the fitness tracking device 100 may include an altimeter. In the case where the fitness tracking device 100 may not include an altimeter or barometer, an altimeter or barometer of the companion device 300 may collect altitude or relative altitude information, and the fitness tracking device 100 may receive the altitude or relative altitude information via interface module 240 (FIG. 2) from the companion device 300.

In another example, the fitness tracking device 100 may not include a temperature sensor, as opposed to an alternative embodiment in which the fitness tracking device 100 may include a temperature sensor. In the case where the fitness tracking device 100 may not include a temperature sensor, a temperature sensor of the companion device 300 may collect temperature information of at least one the ambient temperature proximate to the user and the user's body temperature, and the fitness tracking device 100 may receive the temperature information via interface module 240 (FIG. 2) from the companion device 300.

Figure 4:
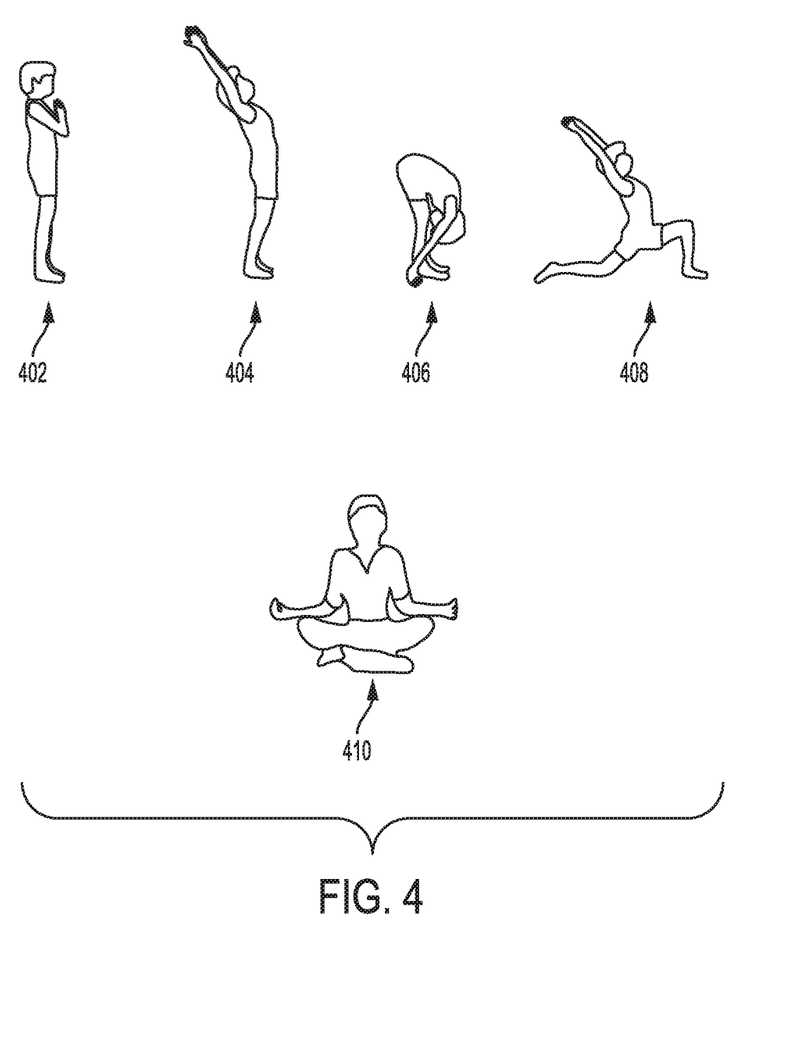
FIG. 4 is a diagram showing yoga poses, according to some embodiments of the present disclosure.

FIG. 4 is a diagram showing yoga poses, according to some embodiments of the present disclosure.

In general, there are four main styles of yoga relevant for calorimetry purposes: power/Vinyasa yoga (also referred to herein as power yoga), wellness yoga, hot/Bikram® yoga (also referred to herein as hot yoga), and meditative/restorative yoga (also referred to herein as meditative yoga). Power yoga is usually characterized by fluid motion between different poses. For example, with reference to FIG. 4, in power yoga each of the poses 402, 404, 406, and 408 are continuous and flow from one pose to the next. Of the four main styles of yoga, power yoga is the most similar to other high intensity activities such as running, cycling or swimming in terms of users' heart rate-energy expenditure profiles. As used herein, power yoga can also refer to Vinyasa, Ashtanga, or Acro yoga.

Wellness yoga consists of a disconnected series of poses. For example, each of the poses 402, 404, 406, and 408 may be held for a certain amount of time and brief breaks may be inserted after each pose. As used herein, wellness yoga can also refer to Hatha, Iyengar, Anasura, Jivamukti, Forrest, Sivananda, or Svaroopa yoga.

Similar to wellness yoga, hot yoga usually also consists of a series of disconnected poses. Unlike wellness yoga, hot yoga is usually practiced in a room with higher temperatures and humidity (e.g., a temperature of approximately 90 to 105 degrees Fahrenheit, and a humidity of approximately 40%). As used herein, hot yoga can also refer to Bikram Yoga®. As explained in more detail below, temperature in a hot yoga room can affect a calorimetry model, since the rise in heart rate may not be correlation to the actual intensity.

Meditative yoga usually involves little to no movement or slow movements. Pose 410 is an example of a meditative yoga pose. As used herein, meditative yoga can also refer to Vini, Kundalini, Integral, or Tantra yoga.

As described in more detail below, there are two factors during a yoga session that can disturb a linear relationship that normally exists between heart rate and energy expenditure during exercise: (1) temperature of a yoga studio and (2) yoga positions, including movement between yoga positions. For example, power yoga is usually associated with an energy expenditure greater than 4 METs, and fitness and hot yoga is usually associated with an energy expenditure of approximately 2.5 METs. Briefly, measured motion data and temperature data can be used to account for the variations in heart rate that deviate from the linear relationship that is normally observed for high intensity exercises.

Figure 5:
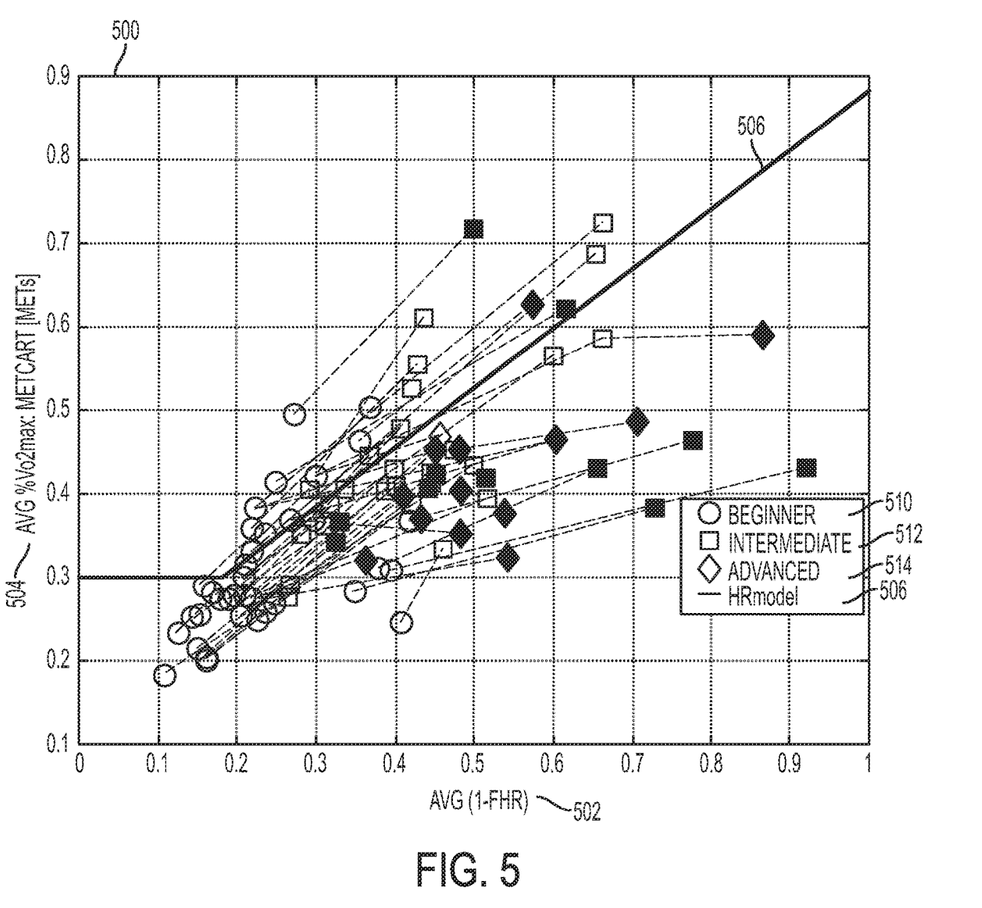
FIG. 5 is a graph 500 showing a relationship between beginning, intermediate and advanced users' energy expenditure and heart rate during a yoga session, according to some embodiments of the present disclosure.

FIG. 5 is a graph 500 showing a relationship between beginning, intermediate and advanced users' energy expenditure and heart rate during a yoga session, according to some embodiments of the present disclosure. The graph 500 includes two axis: average fractional heart rate measurements 502 and average percentage of VO2max measurements 504. The graph also shows a heart rate model 506, beginning user data points 510, intermediate user data points 512, and advanced user data points 514.

The filled in data points are associated with data points for which the amount of $CO_2$ that a user's body expels is much greater than the amount of $O_2$ begin consumed. When this occurs, it likely implies that the subject cannot satisfy their energy dependency operates in an anaerobic state.

Each of the beginning user data points 510, intermediate user data points 512, and advanced user data points 512 show a user's measured average percentage of VO2max measurements 504 at a certain average fractional heart rate 502. Average fractional heart rate 502 is used, in some embodiments, to develop a model that is applicable to the entire population and over all different fitness groups. A user's average percentage of VO2max 504 can be used to calculate a corresponding MET value. An average percentage of VO2max measurements 504 is used, in some embodiments, to create a general model for the entire population. As shown in the graph 500, the correlation between a user's VO2max measurements 504 and heart rate does not follow a typical heart rate model 506 that can normally be assumed during a high intensity workout. For example, a typical heart rate model 506 may linearly relate energy expenditure and HR for FHR<0.6. Typical heart rate models 506 at lower HRs close to resting have difficulty predicting energy expenditure since there is no simple relationship between heart rate and energy expenditure at lower HRs. As described above, two of the major reasons for this skewed correlation are that yoga involves poses where the body is contracted and heart rate increases without a correlated increase in energy expenditure, and the high temperatures associated with some types of yoga increase heart rate also without a correlated increase in energy expenditure. As shown in the graph 500, the amount of skew in the correlation for beginning, intermediate, and advanced users can also vary, respectively. In some embodiments, a user's level can be determined by the speed and number of repetitions the subjects performed. In some embodiments, a user's skill level can be determined by comparing a user's observed work rate. As described in more detail in FIG. 5 and the accompanying text, motion sensor data and ambient temperature data can be used to adjust heart rate data to account for varying yoga styles and yoga postures.

Figure 6:
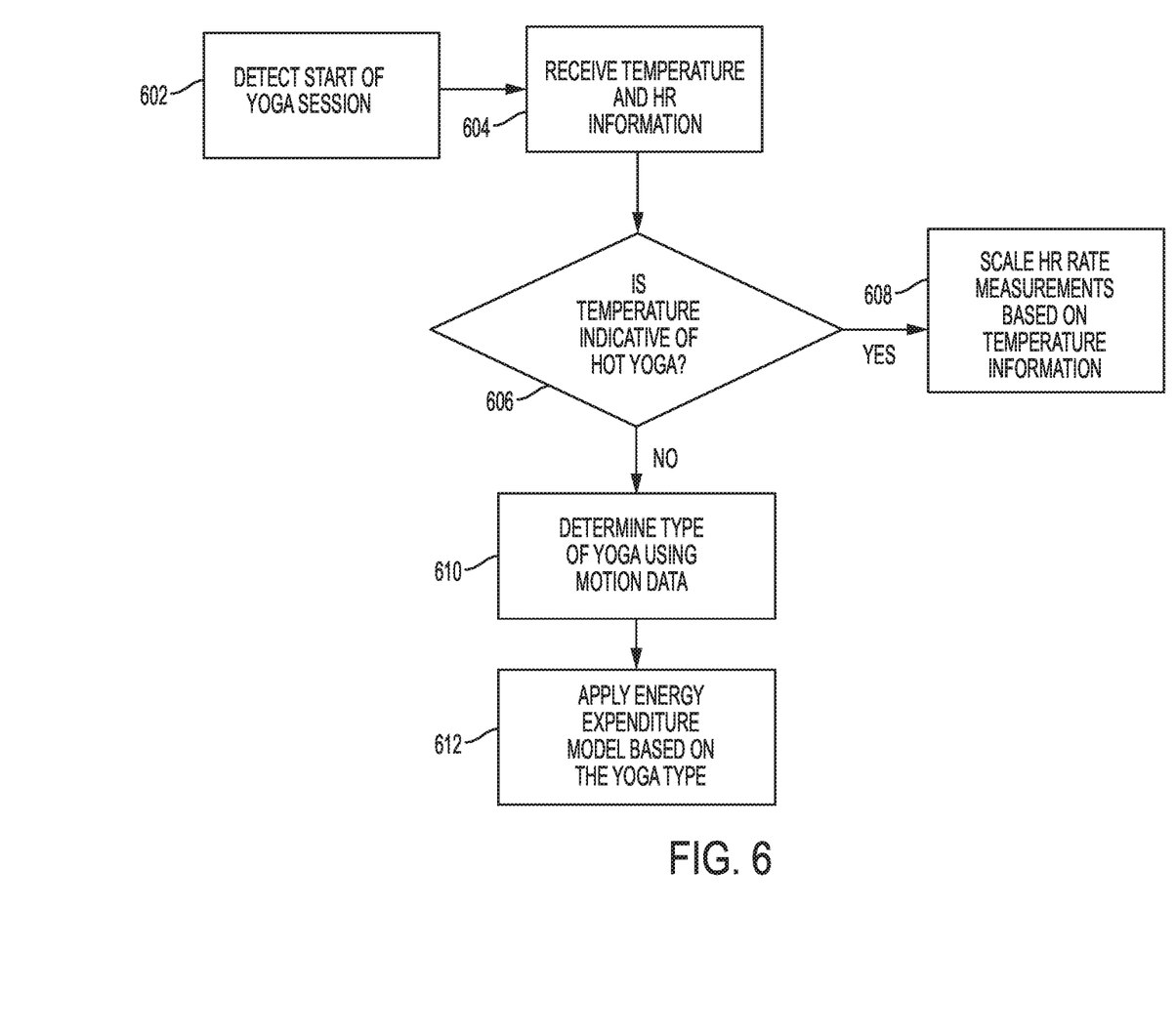
FIG. 6 is a flowchart showing the calculation of a user's energy expenditure during a yoga session, according to some embodiments of the present disclosure.

FIG. 6 is a flowchart showing the calculation of a user's energy expenditure during a yoga session, according to some embodiments of the present disclosure.

Referring to step 602, the start of a yoga session is detected. The start of the yoga session can be indicated based on receiving an instruction from a user from one of the fitness tracking device 100 or the companion device 300. The instruction from the user can be one of indicating the start of a yoga session at a particular time, or the start of a yoga session based on a schedule. The start of the yoga session can also be indicated based on receiving location data from one of the motion sensing module 220 of the fitness tracking device 100 or location data from the companion device 300. For example, at least one of the fitness tracking device 100 and the companion device 300 may be in communication with a map server or other database noting the location of a yoga studio. In some embodiments, the start of a yoga session is not detected until the fitness tracking device 100 confirms that the user is at the yoga studio (e.g., by receiving additional data associated with communications between one of the user's devices with a device of the studio, or confirmation that the yoga studio is a yoga studio frequented by the user using pre-stored data).

Referring to step 604, heart rate information and temperature information is received. As explained above, heart rate information can be received from at least one of a heart rate sensing module 210 of a fitness tracking device 100 or from a companion device 300. Also described above, the heart rate information can include a heart rate measured at various time intervals. Temperature information can also be received from at least one of a heart rate sensing module 210 of a fitness tracking device 100 or from a companion device 300, as described above. The temperature information can be indicative of at least one of a user's body temperature and an ambient temperature proximate to either the fitness tracking device 100 or the companion device 300. The temperature information can be taken at either preset intervals (e.g., every second, minute, hour) or upon a specific request from the user.

Referring to step 606, the fitness tracking device 100 determines whether the yoga session is a hot yoga session. In some embodiments, the companion device 300 makes this determination. A hot yoga session can be detected based on a change of ambient temperature during the yoga session and the ambient temperature prior to the yoga session. In some embodiments, detecting the change in ambient temperature includes determining that the temperature change has exceeded a threshold (e.g., more than 20 degrees Fahrenheit) within a time period proximate to the start of a yoga session (e.g., a 1 minute, 5 minute, or 10 minute interval around the start time of the yoga session). In some embodiments, determining the start of a hot yoga session using temperature information includes detecting that the ambient temperature information is above a threshold value (e.g., more than 100 degrees Fahrenheit). In some embodiments, detecting that the ambient temperature information is above a threshold value includes detecting that the ambient temperature over a range of time (e.g., 1 minute, 5 minute, or 10 minute interval around the start time of the yoga session) is above a threshold value. In some embodiments, a change in humidity can also indicate the start of a yoga session. For example, the humidity level in a hot yoga room is generally higher than the humidity level outside of the yoga room.

Referring to step 608, if the fitness tracking device 100 determines that the yoga session is a hot yoga session, heart rate measurements are scaled to account for the higher temperature. Instead of using a minimum HR to estimate a baseline FHR, in some embodiments, the FHR is estimated with an already elevated HR, which is likely elevated at the start of the session due to the high temperatures.

Referring to step 610, if the fitness tracking device 100 determines that the yoga session is not a hot yoga session, the fitness tracking device 100 determines a type of yoga associated with the yoga session based on motion data. As described above, different types of yoga are associated with different poses or different timings between poses. For example, if the motion data indicates continuous movement throughout the yoga session, then the type of yoga is likely power yoga. If the motion data indicates motion data interspersed with little motion, then the type of yoga is likely wellness yoga. If the motion data indicates very little movement or long periods of little movement, then the type of yoga is likely meditative yoga. A detected low HR can also indicate a meditative yoga session.

Referring to step 612, an energy expenditure model is applied based on the determined yoga type.

For example, if the motion data indicates that a user is practicing power yoga, then the measured heart rate is used, since measured heart rate linearly predicts energy expenditure for high intensity workouts. Additionally, different poses or sets of poses (sequence) are assigned different energy expenditure weights based on difficulty. Once a pose or sequence is detected, the associated energy expenditure weight is assigned to the user. In some embodiments pose energy expenditure is normalized so it can be applicable to all skill levels.

If the motion data indicates that a user is practicing meditative yoga, the energy expenditure is calculated using pre-stored characteristics of the user. For example, a basal metabolic rate can be used as a floor energy expenditure value.

If the motion data indicates that a user is practicing wellness yoga, a pose or series of poses is detected by applying a pose detection algorithm to the motion data. For example, the algorithm can use a combination of the accelerometer and gyro features to estimate the orientation of the device through space and use the pitch, yaw and roll features to help determine the pose. The user acceleration can then be used to help understand the intensity of the pose or the speed at which a user is doing the exercise. For example, high frequency in the accelerometer data can be indicative of resistance in a user's muscles hinting that they are in a position that is either difficult for them or that requires a considerable amount of strength in the arms. Based on the detected pose, energy expenditure can be assigned to the pose based on a difficulty level of the pose and duration of the pose. In some embodiments, a difficulty level is assigned for each of the well-known yoga poses. This information can be stored in a database that can be accessed by the processor of the fitness tracking device 100. In some embodiments, the fitness tracking device 100 can create a new entry for an unknown pose and assign a difficultly level to the unknown pose based on a user's metrics for a known pose similar to the unknown pose.

For example, assume that the fitness tracking device 100 determines that a user is holding a downward dog pose for 30 seconds. The energy expenditure calculated for this pose is approximately 3.5 Mets. As another example, assume that the fitness tracking device 100 determines that a user is holding a warrior pose for 30 seconds. The energy expenditure calculated for this pose is approximately 2 Mets.

In some embodiments, heart rate is also monitored during the wellness yoga poses and can be used to quantify a user's efficiency at the pose and provide a calibration based on the user's efficiency. In general, the more efficient a user is at any physical activity, the less energy he or she expends during the physical activity.

In some embodiments, the wearable device can detect an end of the yoga session. Then a total energy expenditure of the user during the yoga session can be calculated and outputted.

Figure 7A:
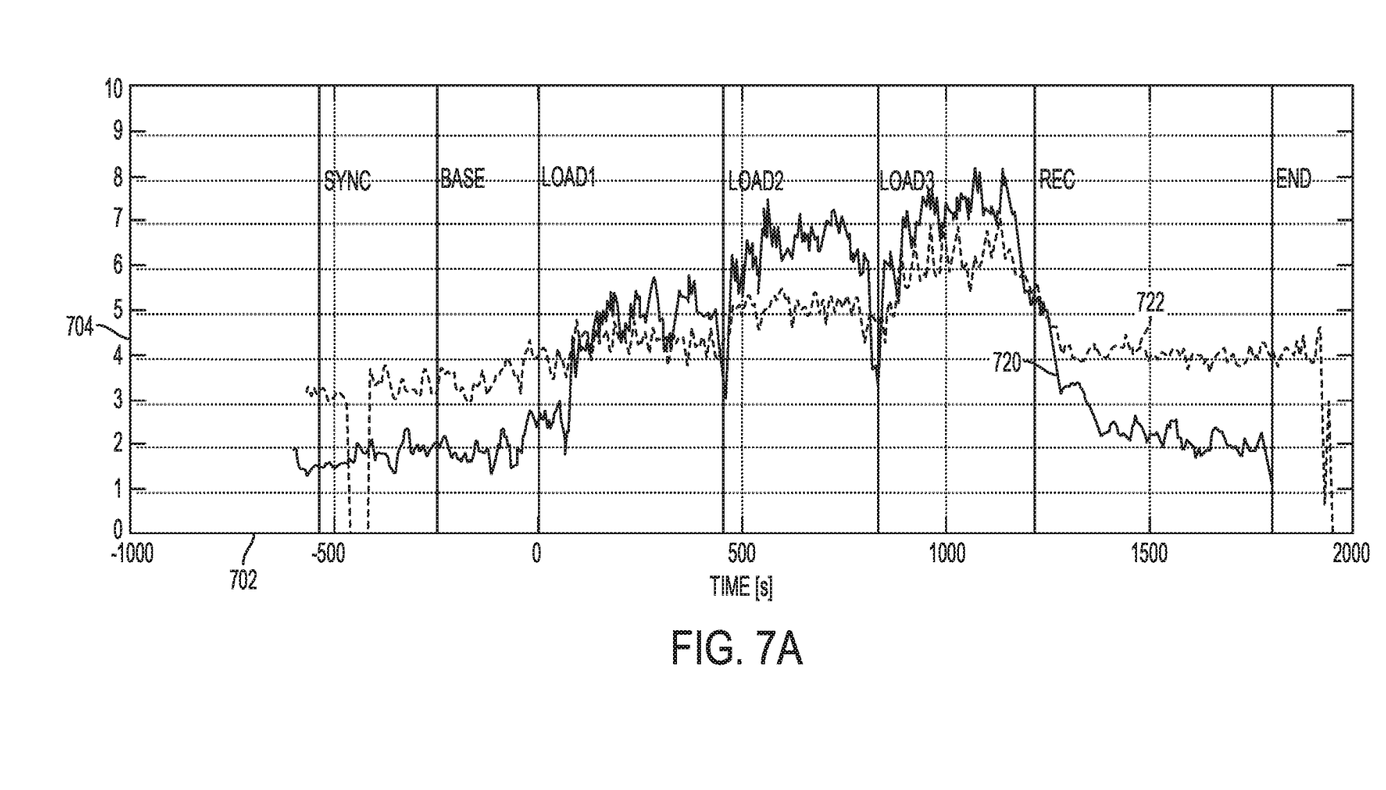
FIGS. 7A-7C are graphs showing a correlation between sensor data and METs, according to some embodiments of the present disclosure.
Figure 7B:
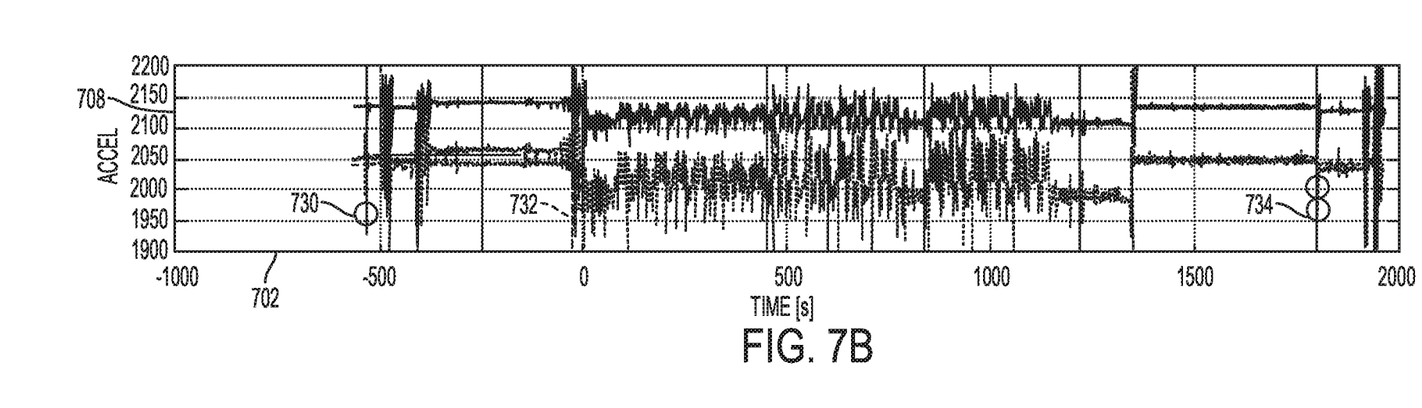
Figure 7C:
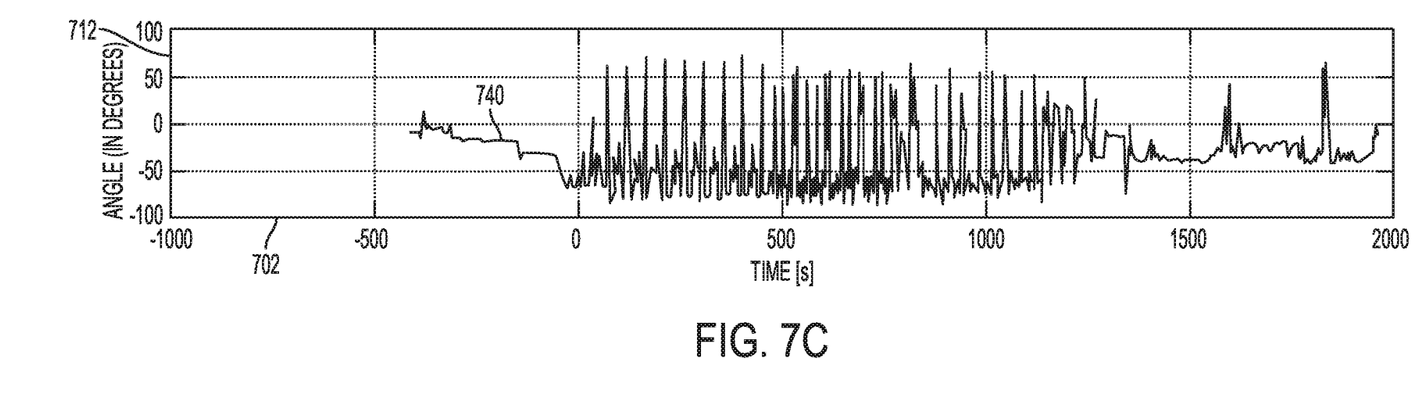

FIGS. 7A-7C are graphs showing a correlation between sensor data and METs, according to some embodiments of the present disclosure.

FIG. 7A is a graph showing METs 704 versus time 702, according to some embodiments of the present disclosure. Line 720 is a plot of METs versus time 702 and line 722 is a plot of HR 722 versus time.

FIG. 7B is a graph showing acceleration 708 versus time 706, according to some embodiments of the present disclosure. In some embodiments, the acceleration data is recorded at the wrist for the participant. 730, 732, and 734 show exercise cycles.

FIG. 7C is a graph showing angle 712 versus time 702, according to some embodiments of the present disclosure. In some embodiments, angle 712 is a pose angle which can be helpful in understanding if the arm is pointing at, under or above the horizon, for example, for detecting poses like sun salutation or downward dog.

As shown in the three graphs taken together, HR and METs increase as the difficulty increases which is also related to the speed at which the user is performing the exercises. Both HR and acceleration graphs show the exercise cycles. From the acceleration data, it is evident that the signatures are separable for the different poses.

In some embodiments, systems and methods are disclosed for determining an amount of calories expended by a user while practicing yoga. In some embodiments, the systems and methods comprise determining, by a computing device worn by a user, a start of a yoga session associated with the user, the computing device comprising a heart rate sensor, a motion sensor, a temperature sensor and a processor; determining, by the computing device, a type of yoga associated with the session based on a temperature difference between a temperature associated with the yoga session and a temperature prior to the yoga session, the type of yoga comprising power yoga, wellness yoga, hot yoga and meditative yoga; determining, by the computing device, heart rate data and motion data associated with the user during the yoga session; and calculating, by the computing device, an energy expenditure for the user associated with the yoga session based on: a default value when the type of yoga comprises meditative yoga, and an expenditure value based on the heart rate data and the motion data when the type of yoga comprises power yoga, wellness yoga, and hot yoga.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processor of any kind of digital computer. Generally, a processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of nonvolatile memory, including by way of example semiconductor memory devices, (e.g., EPROM, EEPROM, and flash memory devices); magnetic disks, (e.g., internal hard disks or removable disks); magneto optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back end component (e.g., a data server), a middleware component (e.g., an application server), or a front end component (e.g., a client computer having a graphical user interface or a web browser through which a user can interact with an implementation of the subject matter described herein), or any combination of such back end, middleware, and front end components. The components of the system can be interconnected by any form or medium of digital data communication, e.g., a communication network. Examples of communication networks include a local area network ("LAN") and a wide area network ("WAN"), e.g., the Internet.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods, and systems for carrying out the several purposes of the disclosed subject matter. It is important, therefore, that the claims be regarded as including such equivalent constructions insofar as they do not depart from the spirit and scope of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter.

What is claimed is:

1. A method for improving the accuracy of a wearable device while calculating an energy expenditure of a user practicing yoga, the method comprising:
   detecting, by a processor circuit of the wearable device, a start of a yoga session;
   measuring, by a heart rate sensing module of the wearable device, a heart rate of the user, wherein the heart rate sensing module comprises a photoplethysmogram (PPG) sensor and the PPG sensor is configured to be worn adjacent to the user's skin;
   measuring, by a temperature sensing module of the wearable device, an ambient temperature;
   collecting, by a motion sensing module of the wearable device, motion data of the user;
   determining, by the processor circuit, a type of yoga practiced by the user based on the measured ambient temperature and the collected motion data;
   selecting, by the processor circuit, an energy expenditure model associated with the determined type of yoga;
   detecting, by the processor circuit, an end of the yoga session;
   calculating, by the processor circuit, an energy expenditure of the user based on at least the measured heart rate and the selected energy expenditure model; and
   outputting, by the processor circuit, the calculated energy expenditure of the user during the yoga session.

2. The method of claim 1, wherein detecting a start of a yoga session comprises receiving an instruction from the user.

3. The method of claim 1, wherein detecting a start of a yoga session comprises:
   receiving location data of the wearable device;
   comparing the received location data with a pre-determined location; and
   detecting the start of a yoga session based upon comparing the received location data and the pre-determined location.

4. The method of claim 1, wherein determining a type of yoga practiced by the user comprises:
   measuring, by the temperature sensing module, a first ambient temperature prior to the start of the yoga session;
   measuring, by the temperature sensing module, a second ambient temperature within a pre-defined time period proximate to the start of the yoga session;
   determining, by the processor circuit, a change of ambient temperature between the first ambient temperature and the second ambient temperature;
   comparing, by the processor circuit, the change of ambient temperature with a pre-defined temperature change threshold; and
   determining, by the processor circuit, the user is practicing hot yoga if the change of ambient temperature is greater than the pre-defined temperature change threshold.

5. The method of claim 4, wherein the pre-defined temperature change threshold is substantially 20 degrees Fahrenheit.

6. The method of claim 1, wherein determining a type of yoga practiced by the user comprises:
comparing, by the processor circuit, the measured ambient temperature with a pre-defined temperature threshold; and
determining, by the processor circuit, the user is practicing hot yoga if the measured ambient temperature is greater than the pre-defined temperature threshold.

7. The method of claim 6, wherein the pre-defined temperature threshold is substantially 100 degrees Fahrenheit.

8. The method of claim 1, wherein determining a type of yoga practiced by the user comprises:
measuring a humidity by a humidity sensing module of the wearable device;
comparing, by the processor circuit, the measured humidity with a pre-determined humidity threshold; and
determining, by the processor circuit, the user is practicing hot yoga if the measured humidity is greater than the pre-determined humidity threshold.

9. The method of claim 1, wherein calculating an energy expenditure of the user comprises calculating the energy expenditure based on the time period between the start of the yoga session and the end of the yoga session.

10. The method of claim 1, wherein the type of yoga comprises power yoga, wellness yoga, hot yoga, or meditative yoga.

11. The method of claim 1, wherein the motion sensing module comprises at least one of an accelerometer, a gyroscope, and a magnetometer.

12. A system for improving the accuracy of a wearable device while calculating an energy expenditure of a user practicing yoga, the system comprising:
a heart rate sensing module configured to measure a heart rate of the user, wherein the heart rate sensing module comprises a photoplethysmogram (PPG) sensor and the PPG sensor is configured to be worn adjacent to the user's skin;
a temperature sensing module configured to measure an ambient temperature;
a motion sensing module configured to collect motion data of the user;
a processor circuit in communication with the heart rate sensing module, the temperature sensing module, and the motion sensing module, the processor circuit configured to execute instructions causing the processor circuit to:
detect a start of a yoga session;
determine a type of yoga practiced by the user based on the measured ambient temperature and the collected motion data;
select an energy expenditure model associated with the determined type of yoga;
detect an end of the yoga session;
calculate an energy expenditure of the user based on at least the measured heart rate and the selected energy expenditure model; and
output the calculated energy expenditure of the user.

13. The system of claim 12, wherein the instructions further cause the processor circuit to receive an instruction from the user indicating a start of the yoga session.

14. The system of claim 12, wherein the instructions further cause the processor circuit to:
receive location data of the wearable device;
compare the received location data with a pre-determined location; and
determine a start of the yoga session based upon comparing the received location data with the pre-determined location.

15. The system of claim 12, wherein:
the temperature sensing module is configured to
measure a first ambient temperature prior to the start of the yoga session, and
measure a second ambient temperature within a pre-defined time period proximate to the start of the yoga session; and
the instructions further cause the processor circuit to
determine a change of ambient temperature between the first ambient temperature and the second ambient temperature,
compare the change of ambient temperature with a pre-defined temperature change threshold, and
determine the user is practicing hot yoga if the change of ambient temperature is greater than the pre-defined temperature change threshold.

16. The system of claim 12, wherein the instructions further cause the processor circuit to:
compare the measured ambient temperature with a pre-defined temperature threshold; and
determine the user is practicing hot yoga if the measured ambient temperature is greater than the pre-defined temperature threshold.

17. The system of claim 12, further comprising a humidity sensing module configured to measure a humidity, and wherein the instructions further cause the processor circuit to:
compare the measured humidity with a pre-determined humidity threshold; and
determine the user is practicing hot yoga if the measured humidity is greater than the pre-determined humidity threshold.

18. The system of claim 12, wherein the type of yoga comprises power yoga, wellness yoga, hot yoga, or meditative yoga.

19. The system of claim 12, wherein the motion sensing module comprises at least one of an accelerometer, a gyroscope, and a magnetometer.

20. A mobile device comprising the system of claim 12.

* * * * *